(12) United States Patent
Maeda et al.

(10) Patent No.: US 7,258,686 B2
(45) Date of Patent: Aug. 21, 2007

(54) CORNEAL SURGERY APPARATUS

(75) Inventors: Naoyuki Maeda, Minoo-shi (JP);
Masaki Tanaka, Okazaki-shi (JP)

(73) Assignee: Nidek Co., Ltd. (JP)

( * ) Notice: Subject to any disclaimer, the term of this patent is extended or adjusted under 35 U.S.C. 154(b) by 0 days.

(21) Appl. No.: 10/755,440

(22) Filed: Jan. 13, 2004

(65) Prior Publication Data
US 2004/0143246 A1 Jul. 22, 2004

(30) Foreign Application Priority Data
Jan. 15, 2003 (JP) ............................ 2003-006929

(51) Int. Cl.
*A61F 9/008* (2006.01)

(52) U.S. Cl. .......................................... 606/5; 606/10

(58) Field of Classification Search ................. 606/4–6
See application file for complete search history.

(56) References Cited

U.S. PATENT DOCUMENTS

| | | | |
|---|---|---|---|
| 4,848,340 A | 7/1989 | Bille et al. | |
| 5,507,799 A | 4/1996 | Sumiya | |
| 5,520,679 A | 5/1996 | Lin | |
| 5,562,656 A | 10/1996 | Sumiya | |
| 5,620,436 A | 4/1997 | Lang et al. | |
| 5,632,742 A | 5/1997 | Frey et al. | |
| 5,637,109 A | 6/1997 | Sumiya | |
| 5,782,822 A * | 7/1998 | Telfair et al. ................... | 606/5 |
| 5,827,264 A | 10/1998 | Hohla | |
| 5,865,832 A * | 2/1999 | Knopp et al. ................. | 606/10 |
| 6,033,075 A | 3/2000 | Fujieda et al. | |
| 6,099,522 A * | 8/2000 | Knopp et al. ................. | 606/10 |
| 6,159,202 A | 12/2000 | Sumiya et al. | |
| 6,203,539 B1 | 3/2001 | Shimmick et al. | |
| 6,210,401 B1 | 4/2001 | Lai | |
| 6,494,878 B1 * | 12/2002 | Pawlowski et al. ............ | 606/4 |
| 6,579,282 B2 * | 6/2003 | Bille et al. ...................... | 606/5 |
| 6,585,724 B2 * | 7/2003 | Toh ................................ | 606/5 |
| 6,607,527 B1 * | 8/2003 | Ruiz et al. .................... | 606/41 |
| 6,655,805 B2 | 12/2003 | Fujieda | |
| 6,666,857 B2 * | 12/2003 | Smith .......................... | 606/12 |
| 6,702,806 B2 * | 3/2004 | Gray et al. ..................... | 606/5 |
| 6,702,809 B1 * | 3/2004 | Knopp et al. ................. | 606/10 |
| 7,044,602 B2 * | 5/2006 | Chernyak .................... | 351/208 |

(Continued)

FOREIGN PATENT DOCUMENTS

WO WO 01/28476 A1 4/2001

*Primary Examiner*—Henry M Johnson, III
(74) *Attorney, Agent, or Firm*—Rader Fishman & Grauer PLLC; Ronald P. Kananen

(57) ABSTRACT

A corneal surgery apparatus capable of irradiating a laser beam at a desired position on a cornea more accurately. The apparatus has an optical system for irradiating a laser beam onto a cornea, a unit which moves an irradiation position of the beam relative to an eye, a unit having an element for picking up an image of an anterior-segment, which processes an image signal from the element to detect a characteristic point in the image, a unit which stores positional information on the characteristic point when the eye is in a predetermined reference state, a unit which detects duction condition of the eye based on positional information on the characteristic point when the eye is in a surgery state and that being stored, and a unit which controls the moving unit based on a detection result of the duction detection unit.

2 Claims, 12 Drawing Sheets

U.S. PATENT DOCUMENTS

| | | | |
|---|---|---|---|
| 2002/0013573 A1* | 1/2002 | Telfair et al. | 606/5 |
| 2002/0013576 A1* | 1/2002 | Gray et al. | 606/5 |
| 2002/0082590 A1* | 6/2002 | Potgieter | 606/4 |
| 2002/0082629 A1* | 6/2002 | Cox et al. | 606/166 |
| 2002/0097378 A1* | 7/2002 | Saito et al. | 351/206 |
| 2002/0161356 A1* | 10/2002 | Bille et al. | 606/4 |
| 2003/0144650 A1* | 7/2003 | Smith | 606/5 |
| 2004/0002694 A1* | 1/2004 | Pawlowski et al. | 606/4 |
| 2004/0044333 A1* | 3/2004 | Sugiura | 606/4 |
| 2004/0054359 A1* | 3/2004 | Ruiz et al. | 606/5 |
| 2004/0143244 A1* | 7/2004 | Gray et al. | 606/5 |
| 2004/0199150 A1* | 10/2004 | Lai | 606/5 |

\* cited by examiner

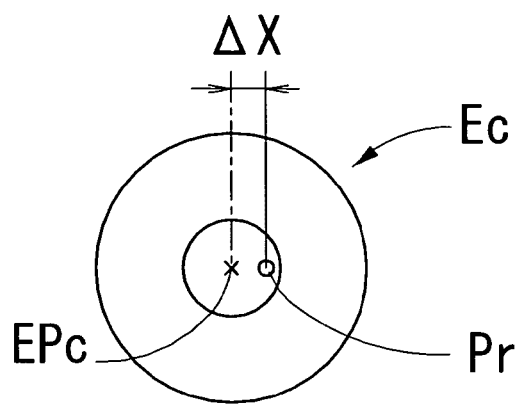
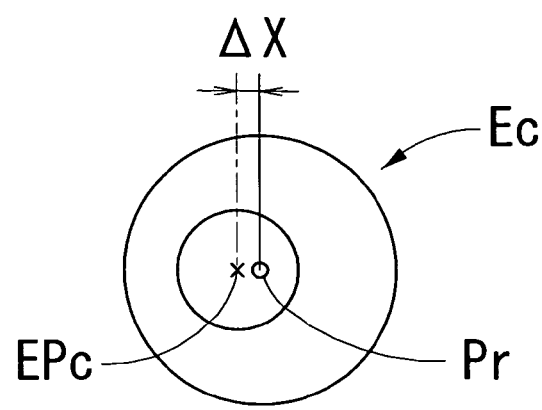
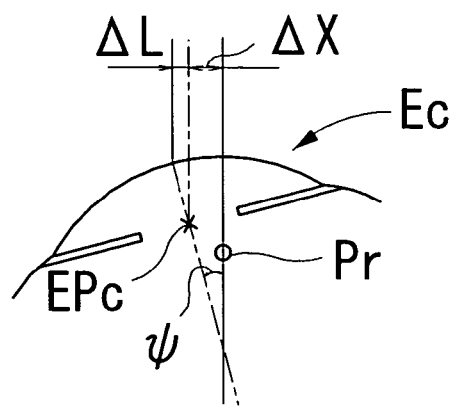
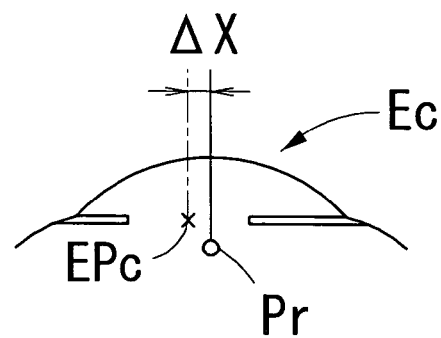
FIG. 14A    FIG. 14B

CORNEAL SURGERY APPARATUS

BACKGROUND OF THE INVENTION

1. Field of the Invention

The present invention relates to a corneal surgery apparatus which ablates a cornea by irradiation of a laser beam.

2. Description of Related Art

Conventionally, there is known a corneal surgery apparatus which ablates a cornea by irradiation of a laser beam and changes a shape of a corneal surface to correct a refractive error of an eye. In many apparatuses of this kind, a patient (a patient's eye) is made fixate on a fixation lamp during a surgery, and a pupil center position of the eye at that time is taken as a reference when alignment of an irradiation position of the laser beam is performed. However, in the case of the patient who is not good at fixation, an eyeball sometimes moves, which leads to difficulty in maintaining accurate alignment. Thus, there is proposed a corneal surgery apparatus which detects the pupil center position based on a picked up image of an anterior-segment of the eye to perform alignment, and in a case where the pupil center position is moved, moves (performs tracking of) the irradiation position in accordance with the movement of the pupil center position to maintain the alignment.

However, in the method of moving the irradiation position with reference to the pupil center position, if there occurs duction in the eye (monocular eyeball movement such as supraduction, infraduction, adduction and abduction), the irradiation position on the cornea is displaced (deviated) due to a height difference between the pupil and the corneal surface. That is to say, as shown in FIG. 4, a position P is a position on the cornea corresponding to the pupil center position EPc detected in the image-pickup direction (Z direction) when the eye is horizontally positioned (is in a reference state), while a position Pd is a position on the cornea corresponding to the pupil center position EPc detected in the image-pickup direction when the duction occurs, which is displaced (deviated) by an amount of ΔL. In order to perform accurate keratorefractive surgery, it is desired that the laser beam be irradiated with reference to a given position on the cornea.

SUMMARY OF THE INVENTION

An object of the invention is to overcome the problems described above and to provide a corneal surgery apparatus capable of irradiating a laser beam at a desired position on a cornea more accurately.

To achieve the objects and in accordance with the purpose of the present invention, a corneal surgery apparatus has an irradiation optical system for irradiating a laser beam onto a cornea of a patient's eye, a moving unit which moves an irradiation position of the laser beam by the irradiation optical system relative to the patient's eye, a characteristic point detection unit, having an image-pickup element for picking up an image of an anterior-segment of the patient's eye, which processes an image signal from the image-pickup element to detect a characteristic point in the anterior-segment image, a storage unit which stores positional information on the characteristic point when the patient's eye is placed under a predetermined reference state, a duction detection unit which detects a duction condition of the patient's eye based on positional information on the characteristic point when the patient's eye is placed under a surgery state and the stored positional information on the characteristic point, and a movement control unit which controls the moving unit based on a detection result of the duction detection unit.

In another aspect of the present invention, a corneal surgery apparatus has an irradiation optical system for irradiating a laser beam onto a cornea of a patient's eye, a moving unit which moves an irradiation position of the laser beam by the irradiation optical system relative to the patient's eye, an alignment detection unit which detects an alignment condition of the irradiation position with the patient's eye, a duction detection unit which detects a duction condition of the patient's eye, and a movement control unit which controls the moving unit based on a detection result of the alignment detection unit and a detection result of the duction detection unit.

Additional objects and advantages of the invention are set forth in the description which follows, are obvious from the description, or may be learned by practicing the invention. The objects and advantages of the invention may be realized and attained by the corneal surgery apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

FIGS. 14A and 14B are views describing displacement (deviation) of a pupil center position from a reflex formed by the target projection optical system.

DETAILED DESCRIPTION OF THE PREFERRED EMBODIMENTS

Figure 1:
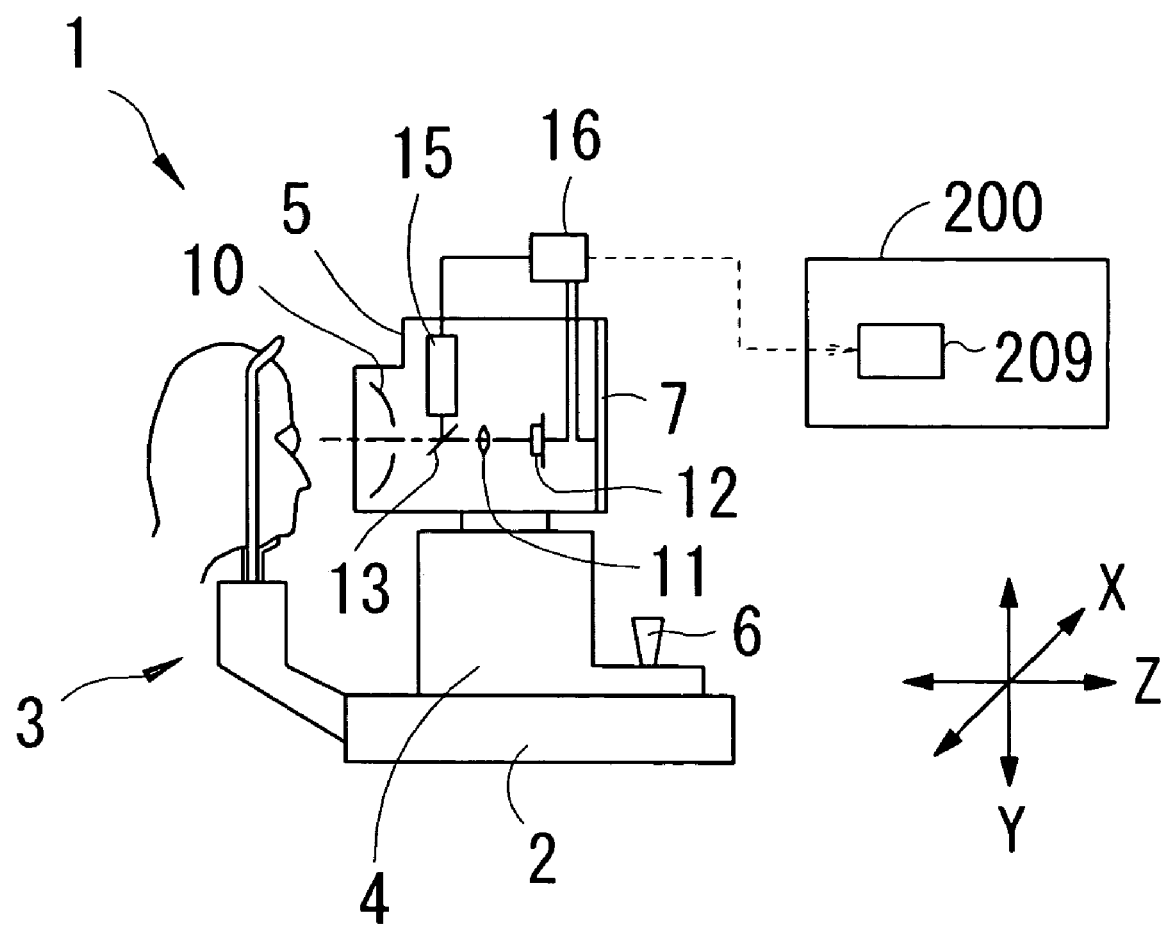
FIG. 1 is a view showing a schematic configuration of a corneal surgery apparatus system consistent with the present invention.

A detailed description of one preferred embodiment of a corneal surgery apparatus embodied by the present invention is provided below with reference to the accompanying drawings. FIG. 1 is a view showing a schematic configuration of a corneal surgery apparatus system consistent with the present invention. An ophthalmic measurement apparatus 1 measures a corneal shape and eye refractive power distribution of a patient's eye. A corneal surgery apparatus 200 irradiates a laser beam onto the patient's eye.

The measurement apparatus 1 is provided with a head support part 3 fixed to a base 2, a moving unit 4 provided horizontally movable on the base 2, a measurement unit 5 provided vertically movable on the moving unit 4, a joystick 6 for operating the movement of the moving unit 4, and a monitor 7 for displaying analytical results (measurement results) and the like. Measurement is performed while a patient's face is placed upright on the head support part 3. Arranged in the measurement unit 5 are optical systems such as a projection optical system 10 for projecting a number of circular placido rings onto a cornea of the patient's eye, a camera unit 12 which picks up, via a lens 11, an image of an anterior-segment of the patient's eye including images of the placido rings projected onto the cornea, a half mirror 13, and an eye refractive power measurement optical system 15. The image picked up by the camera unit 12 and measurement information obtained by the eye refractive power measurement optical system 15 are inputted into an analyzing unit 16. The analyzing unit 16 has a function of obtaining measurement data on the corneal shape and the eye refractive power distribution, respectively, and calculating data on corneal ablation amount distribution based on those measurement data. The camera unit 12 picks up also an image of the anterior-segment onto which the placido rings are not projected. Then, the picked-up image is stored in a memory provided to the analyzing unit 16. The obtained data on the corneal ablation amount distribution and on the image of the anterior-segment are transferred (inputted) to a computer 209 in the surgery apparatus 200 via cable communication or electronic recording medium and are stored in the computer 209.

Figure 2:
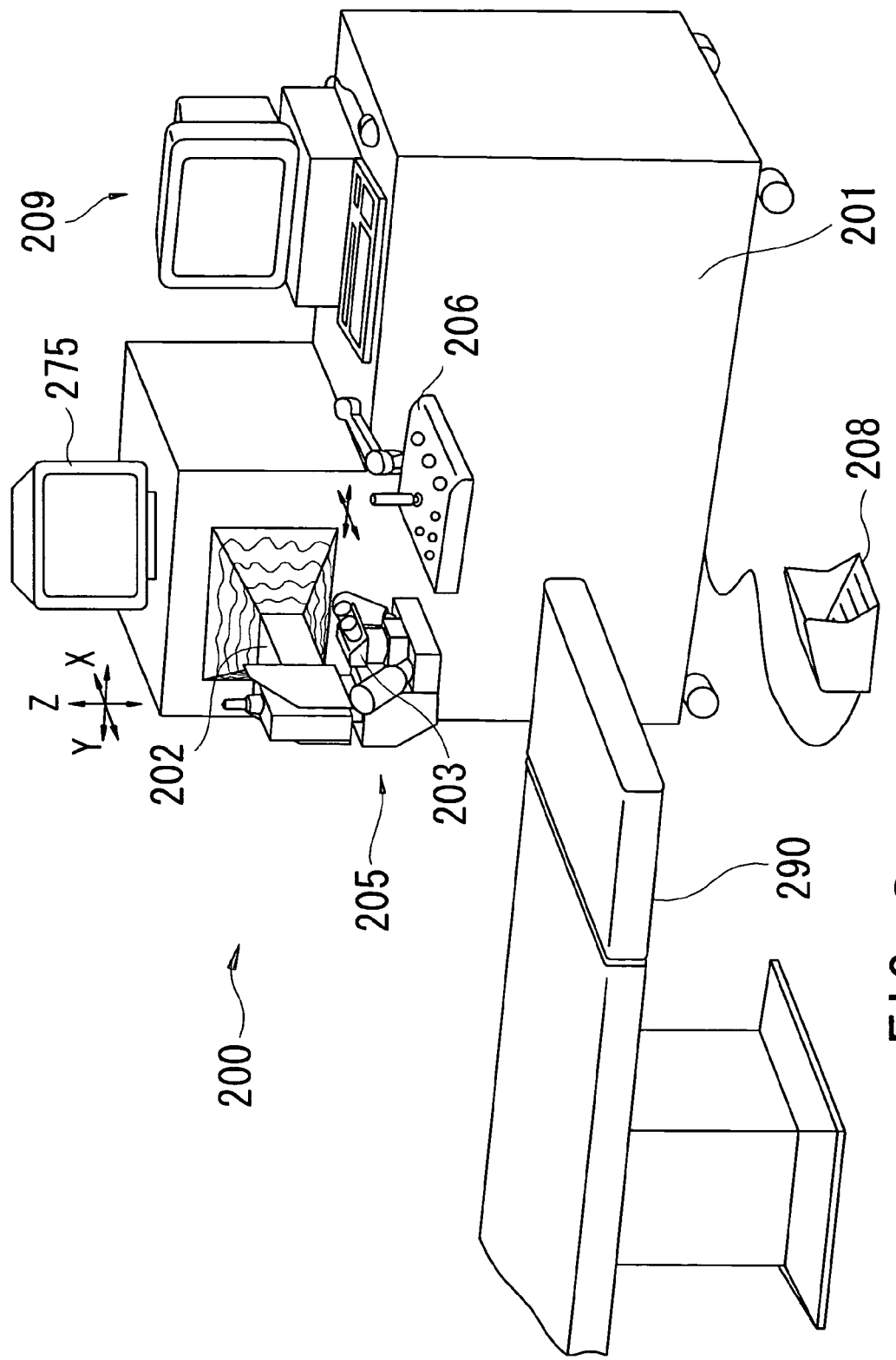
FIG. 2 is a schematic external view of a corneal surgery apparatus.
Figure 3:
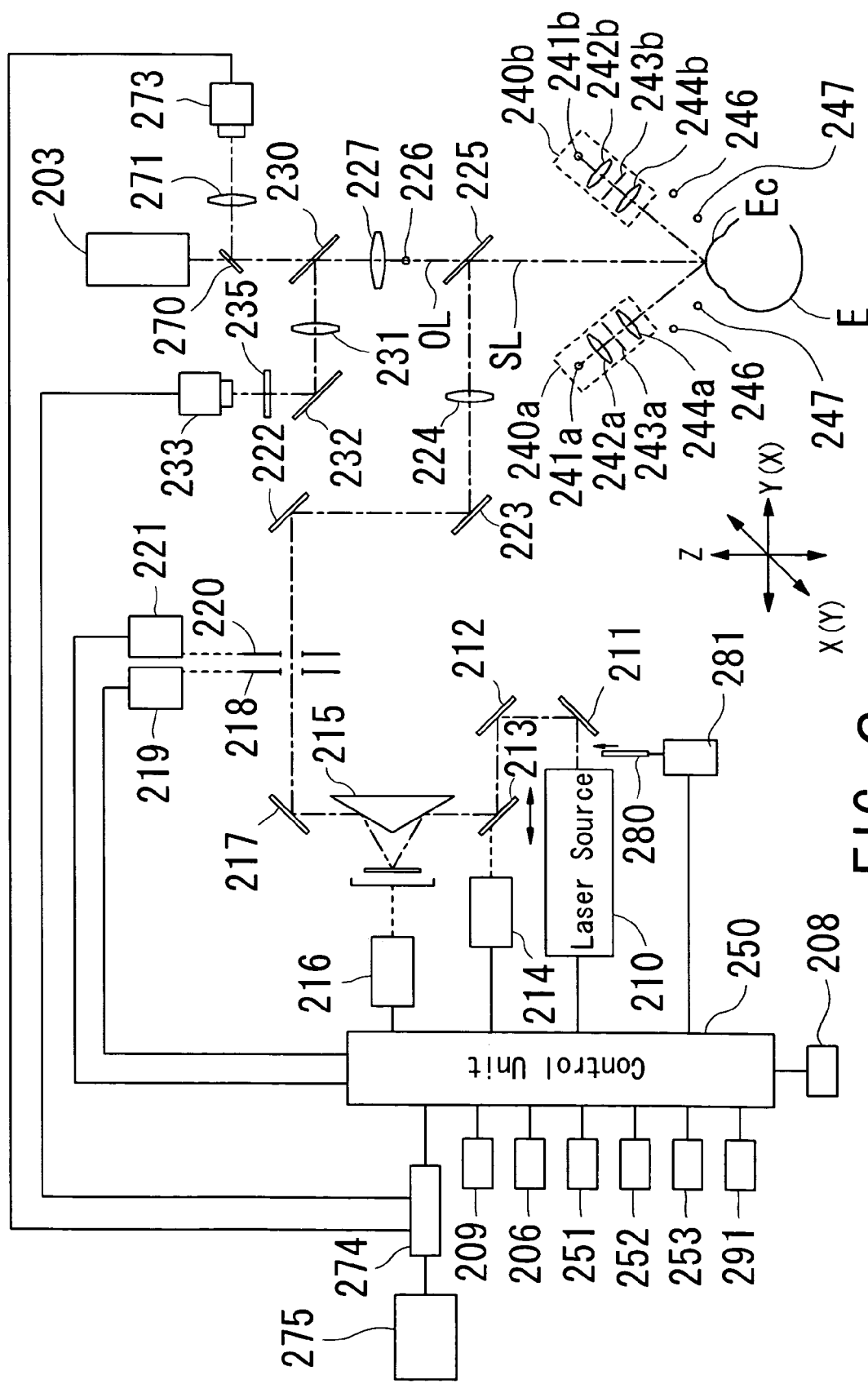
FIG. 3 is a view showing a schematic configuration of a laser irradiation optical system and a control system in the corneal surgery apparatus.
Figure 4:
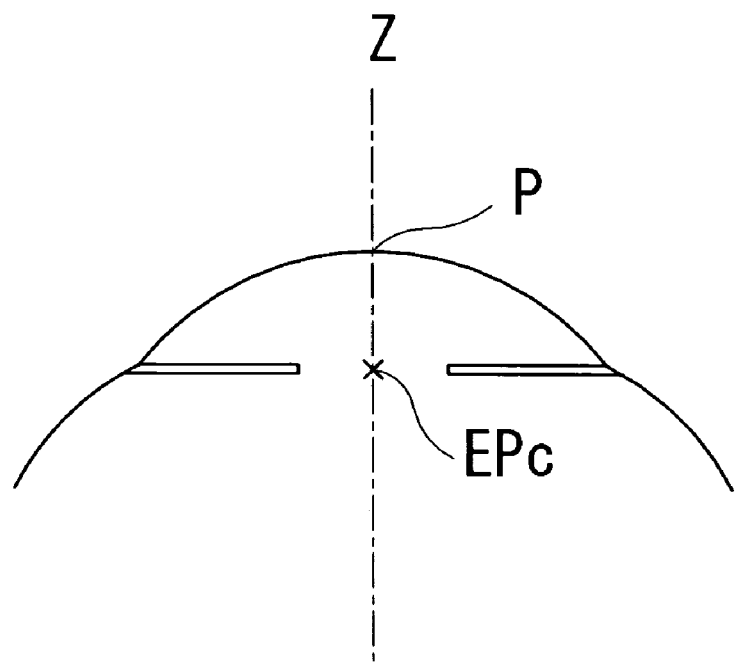
FIG. 4 is a view illustrating displacement (deviation) of a predetermined position on a cornea in the case of duction.
Figure 4:
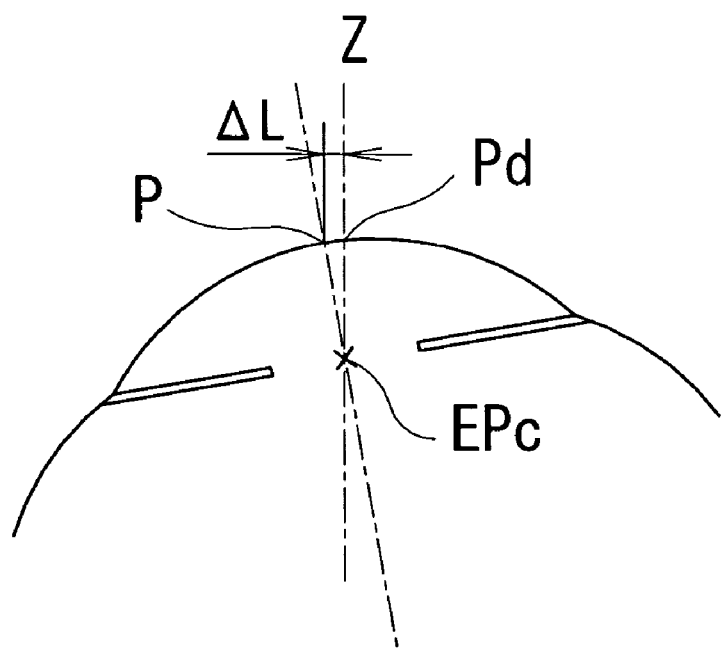

FIG. 2 is a schematic external view of the surgery apparatus 200, and FIG. 3 is a view showing a schematic configuration of a laser irradiation optical system and a control system in the surgery apparatus 200. A laser beam emitted from an excimer laser source 210 disposed inside a main body 201 of the surgery apparatus 200 is transmitted through optical systems such as mirrors and guided to an arm unit 202. The arm unit 202 is movable in a horizontal direction (X and Y directions) shown in FIG. 2. In addition, a tip portion 205 of the arm unit 202 is movable in a vertical direction (a Z direction) The movement in each direction is performed by an X-direction driving unit 251, a Y-direction driving unit 252 and a Z-direction driving unit 253 comprised of a motor, a sliding mechanism and the like. Arranged on a controller 206 are a joystick and various switches. A footswitch 208 transmits a trigger signal for laser irradiation. The computer 209 inputs various data for a necessary surgical condition, and performs calculation, display, storage and the like of data on laser irradiation control. A color monitor (display) 275 displays an image of the patient's eye E for observation. The patient undergoes the surgery while being recumbent (lying on his/her back) on a bed 290. The patient's eye E is placed under a microscope unit 203 attached to the tip portion 205. Besides, the bed 290 is rotatable in the horizontal direction by a bed rotation mechanism 291. Incidentally, the Z direction is a direction of a central optical axis SL of the irradiation optical system (an irradiation reference axis), and the X and Y directions are two-dimensional directions orthogonal to the optical axis SL. In relation to the patient's eye E, the X, Y and Z directions in FIG. 1 correspond to the X, Y and Z directions in FIG. 2.

In FIG. 3, the laser beam emitted from the laser source 210 is reflected by mirrors 211 and 212, and further reflected by a plane mirror 213. The mirror 213 is translatable (movable) in the direction of the arrow shown in FIG. 3 by a mirror driving unit 214, so that the laser beam may be translated (scanned) in the Gaussian distribution direction to uniformly ablate an object. In this regard, Japanese Patent Application Unexamined Publication No. Hei4-242644 corresponding to U.S. Pat. No. 5,507,799 describes in detail.

An image rotator 215 is driven and rotated about the optical axis SL as its center by an imager rotator driving unit 216, and the laser beam is rotated about the optical axis SL. Reference numeral 217 indicates a mirror.

A circular aperture 218 with a circular opening limits an ablation area to a circular shape, and its opening diameter is changed by an aperture driving unit 219. A slit aperture 200 with a slit opening limits the ablation area to a slit shape, and its opening width and opening direction are changed by an aperture driving unit 221. Mirrors 222 and 223 change the direction of the beam. A projection leans 224 is for projecting images of the openings of the circular aperture 218 and the slit aperture 220 onto the cornea Ec of the eye E.

A dichroic mirror 225 has a property of reflecting the excimer laser beam and transmitting visible light and infrared light. The laser beam passed through the projecting lens 224 is reflected by the dichroic mirror 225, and is directed to and irradiated onto the cornea Ec.

Arranged below the dichroic mirror 225 are slit projection optical systems 240a and 240b symmetrical with respect to an optical axis OL of an objective lens 227. The slit projection optical systems 240a and 240b consist of illumination light sources 241a and 241b for emitting visible light, condenser lenses 242a and 242b, slit plates 243a and 243b having a cross-shaped slit, and projecting lenses 244a and 244b, respectively. The slit plates 243a and 243b are in conjugate positional relations with the cornea Ec with respect to the projecting lenses 244a and 244b. Slit images of the slit plates 243a and 243b are arranged to be formed at a focal position of the objective lens 227 on the optical axis OL. The slit projection optical systems 240a and 240b are utilized for alignment in the Z direction. Besides, in the preferred embodiment, the optical axes SL and OL are made coaxial. However, they need not be coaxial so long as they have a predetermined positional relationship.

Placed above the dichroic mirror 225 and on the optical axis OL are a fixation lamp 226, the objective lens 227, a dichroic mirror 230 which reflects the infrared light and transmits the visible light, and the microscope unit 203. The eye E is illuminated by visible light sources 247, and a surgeon observes the eye E through the microscope unit 203. On an optical path on the reflecting side of the dichroic mirror 230, an image forming lens 231, a mirror 232, an infrared light transmission filter 235, and a CCD camera 233 for infrared photographing are sequentially arranged. The camera 233 picks up the image of the anterior-segment illuminated by infrared light sources 246. The output of the camera 233 is connected to an image processing unit 274.

In addition, a half mirror 270 is arranged in a position that is above the dichroic mirror 230 and between binocular paths of the microscope unit 203 (on the optical axis OL). Arranged on an optical path on the reflecting side of the half mirror 270 are an image forming lens 271 and a CCD camera 273 for visible photographing. The camera 273 picks up the image of the anterior-segment illuminated by the visible light source 247. The output of the camera 273 is connected to the image processing unit 274.

A control unit 250 controls the laser source 210 and each of the driving units. The control unit 250 is connected with the computer 209, the image processing unit 274, the controller 206, the footswitch 208 and the like. In addition, reference numeral 280 is a safety shutter, and reference numeral 281 is a driving unit therefor. The control unit 250 controls to insert the safety shutter 280 into the optical path of the laser beam and suspend the laser irradiation in case of trouble and the like.

Ablation performed by the surgery apparatus 200 will be briefly described hereinafter. In the case of ablation for myopic correction so as to remove a spherical component, the ablation is performed in the following manner. The laser beam is moved (scanned) in the Gaussian distribution direction by moving the mirror 213 within the opening of the circular aperture 218. Then, every time the laser beam has been moved (scanned) in one direction, the moving (scanning) direction of the laser beam is changed by the rotation of the image rotator 215, and the ablation is performed within the opening of the circular aperture 218. This is performed every time the opening diameter of the circular aperture 218 is sequentially changed. Thereby, the ablation of the spherical component is performed deeply at a central part of the cornea Ec and shallowly at a peripheral part.

Next, in the corneal surgery apparatus system having a constitution as above, a method for correcting displacement (deviation) of an irradiation position of the laser beam due to duction will be hereinafter described. Here, the alignment (including tracking) is performed with reference to a pupil center position. The description will be given on a case where a duction condition is detected by utilizing marks previously provided to the eye E.

Firstly, the corneal shape and the eye refractive power distribution of the eye E are measured by the measurement apparatus 1. For the measurement, the patient's head is fixed by the head support part 3 so that both eyes of the patient are horizontally positioned (the patient's face is made upright). The eye E is made fixate on a fixation lamp in the eye refractive power measurement optical system 15. The alignment of the eye E with the optical system is completed and the corneal shape and the eye refractive power distribution are respectively measured, then the data on the corneal ablation amount distribution is obtained by the analyzing unit 16. The obtained data on the corneal ablation amount distribution is transferred (inputted) to the surgery apparatus 200.

Figure 5:
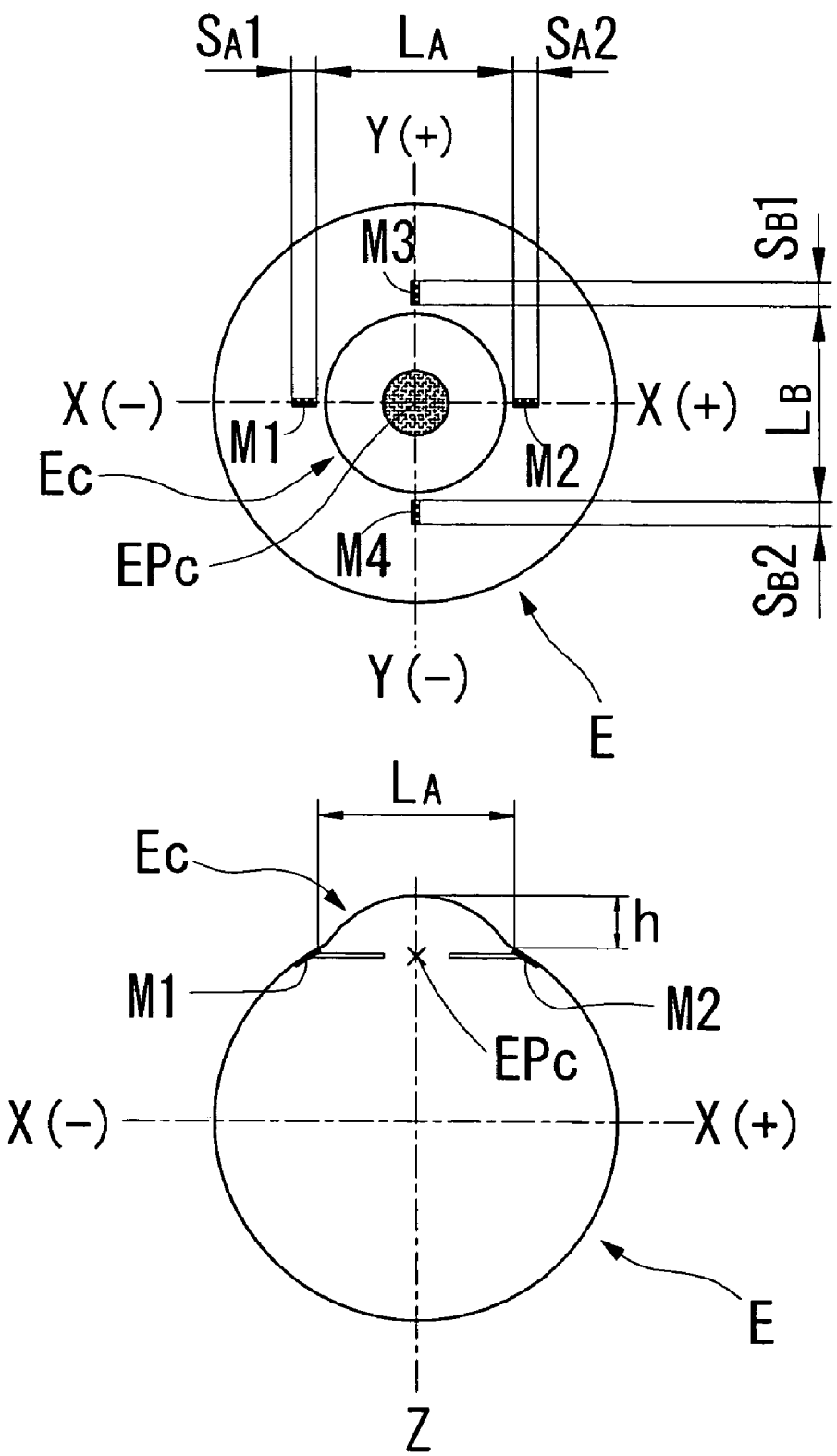
FIG. 5 is a view illustrating marks previously provided to an eyeball of a patient's eye.

Here, marks are previously provided to the eyeball of the eye E before the surgery performed by the surgery apparatus 200. For example, as shown in FIG. 5, four marks M1, M2, M3 and M4 are previously provided. Preferably, the marks M1 to M4 are provided at symmetric positions on a sclera in X and Y directions of an X-Y coordinate system having the cornea Ec therebetween. It is preferable that the marks M1 to M4 have an observable color. Methylene blue as typical dye may be used, but red dye may also be used. In addition, the marks M1 to M4 are preferably rectangular so that change in their lengths in the event of the duction is observable. However, a plurality of marks in a dot shape may be provided in line. Further, the marks M1 to M4 may be provided using an appropriate marking member while observing a slit lamp or the like, moreover, it is preferable to use a marking member in which a positional relationship of the respective marks is uniform.

After providing the marks M1 to M4, the image of the anterior-segment of the eye E is picked up by the measurement apparatus 1. As in the case of the measurement for determining the corneal ablation amount distribution, the image of the anterior-segment provided with the marks M1 to M4 is preferably picked up while the patient's face is fixed by the head support part 3 so that the both eyes are horizontally positioned. Thereby, the image of the anterior-segment including the marks M1 to M4 is picked up by the camera unit 12 under the same condition as the measurement, and stored in the memory of the analyzing unit 16. The image including the marks M1 to M4 obtained at this time is taken as a reference state for correcting the displacement (deviation) of the irradiation position due to the duction.

Then, the data on the image of the anterior-segment including the marks M1 to M4 is transferred (inputted) to the computer 209. The computer 209 processes the image to obtain (detect) and store positional information on the marks M1 to M4 (distances between the marks, distances with respect to the pupil center position, lengths of the respective marks, and the like) in the reference state. Alternatively, the processing may be performed by the measurement apparatus 1, and only the positional information may be transferred (inputted) to the computer 209.

After having the patient lie on the bed 290, the eye E is placed under the microscope unit 203 by moving the tip portion 205, and is made fixate on the fixation lamp 226. The surgeon performs alignment while observing the eye E through the microscope unit 203. Once the pupil position of the eye E becomes observable, automatic alignment and automatic tracking may be performed. The image of the anterior-segment picked up by the camera 233 is inputted into the image processing unit 274, and the pupil center position is detected by the image processing unit 274. In this regard, Japanese Patent Application Unexamined Publication No. Hei9-149914 corresponding to U.S. Pat. No. 6,159, 202 describes in detail. The control unit 250 controls the driving units 251 and 252 based on the detection results of the pupil center position and moves the arm unit 202 in the X and Y directions to align the optical axis SL with the pupil center position. Besides, the alignment in the Z direction is performed so that the two cross-shaped slit images projected onto the cornea Ec from the slit projection optical systems 240a and 240b are superimposed at a corneal vertex position. In this regard, Japanese Patent Application Unexamined Publication No. Hei6-47001 corresponding to U.S. Pat. No. 5,562,656 describes in detail.

In addition, the image of the anterior-segment of the eye E provided with the marks M1 to M4 is picked up by the CCD camera 273, and an image signal thereof is inputted into the image processing unit 274. The image processing unit 274 obtains (detects) positional information on the marks M1, M2, M3 and M4 included in the image of the anterior-segment, and obtains (detects) information on the duction condition of the eye E based on the positional information obtained and the positional information on the marks M1, M2, M3 and M4 in the reference state stored in the computer 209. Incidentally, if photographing magnification of the image of the anterior-segment picked up by the measurement apparatus 1 is different from that of the image of the anterior-segment picked up by the CCD camera 273 to be processed, the magnifications are corrected so that their information are in line with each other.

Hereinafter, description will be given on a method for detecting the duction condition. In the image of the reference state (see FIG. 5), assume that a distance between the marks M1 and M2 (a distance between inner edges of the respective marks) is L$_A$, a distance between the marks M3 and M4 is L$_B$, a length of the mark M1 in the X direction is S$_A$1, a length of the mark M2 in the X direction is S$_A$2, a length of the mark M3 in the Y direction is S$_B$1, and a length of the mark M4 in the Y direction is S$_B$2.

Figure 6:
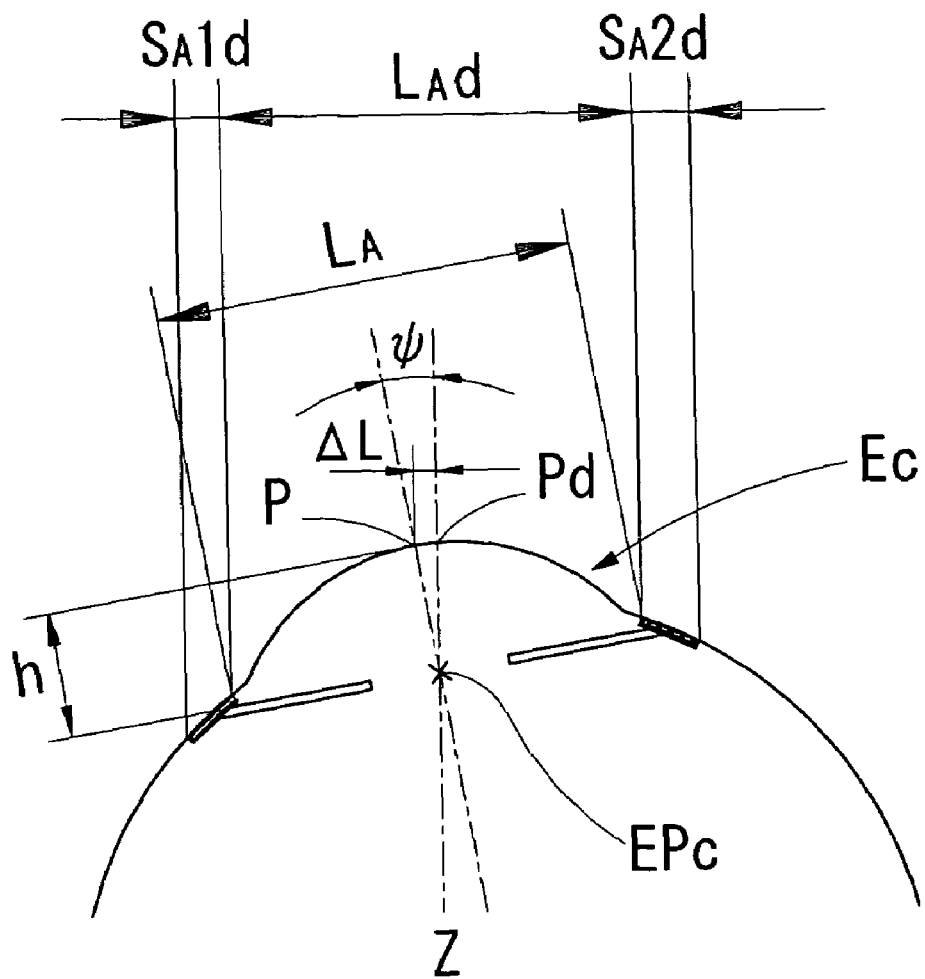
FIG. 6 is a view describing detection of duction condition using the marks.
Figure 7:
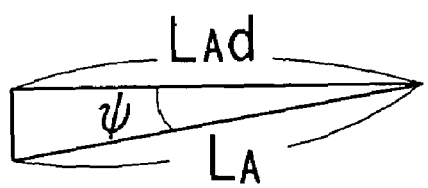
FIG. 7 is a view describing the detection of the duction condition.

Here, with respect to the reference state in FIG. 5, the duction of the eyeball is assumed to occur in an X(−) direction (a left direction in FIG. 5) by an angle ψ as shown in FIG. 6. A position P is a position on the cornea Ec with respect to the pupil center position EPc and is detected in the Z direction when the eyeball is in the reference state. However, when the duction occurs, the position on the cornea Ec with respect to the pupil center position EPc is displaced (deviated) by an amount of ΔL and is detected as a position Pd in the Z direction. Here, due to the duction by the angle ψ, the distance L$_A$ detected in the Z direction is changed to L$_A$d. Concerning L$_A$, ψ and L$_A$d, the relational expression, Formula 1-1 holds (see FIG. 7), by which the duction angle ψ is obtained.

$$\cos \psi = L_Ad/L_A \qquad \text{Formula 1-1}$$

Assuming that a height from an iris surface to the position P on the cornea Ec is h, the displacement (deviation) amount ΔL from Pd to P due to the duction is obtained as Formula 1-2.

$$\Delta L = h \times \sin \psi \qquad \text{Formula 1-2}$$

As to the height h, a mean value is used or a previously measured value is inputted in advance.

In addition, in a case where the duction of the eyeball occurs in the X(−) direction, the lengths S$_A$1 and S$_A$2 of the marks M1 and M2 are changed to S$_A$1d and S$_A$2d, respectively. An inclination direction of the duction may be determined by comparing S$_A$1 and S$_A$1d (or S$_A$2 and S$_A$2d). That is to say, when the duction of the eyeball occurs in the X(−)direction, S$_A$1>S$_A$1d holds, and when the duction of the eyeball occurs in an X(+)direction, S$_A$1<S$_A$1d holds.

In a case where the duction of the eyeball occurs in the Y direction, as in the case of the X direction, the distance L$_B$ between the marks M3 and M4 in the reference state is changed to a distance L$_B$d due to the duction, thereby the displacement (deviation) amount ΔL is obtained. The change in the length S$_B$1 of the mark M3 or the length S$_B$2 of the mark M4 enables determining whether the duction is in Y(−)or Y(+) direction.

In addition, in a case where the duction occurs in a certain direction θ1 on an X-Y plane, the ductions in the X and Y directions mentioned above are combined. This case will be described hereinafter. Here, the duction is assumed to occur, taking an axis N1 in FIG. 8 as a rotation axis, by an angle ψ in a direction of an axis N2 orthogonal to the axis N1. The axis N2 is at an angle θ1 with the X direction. By this duction, detection points Ma1, Ma2, Ma3 and Ma4 of the respective marks are displaced (deviated) to Ma1d, Ma2d, Ma3d and Ma4d, respectively.

Figure 9:
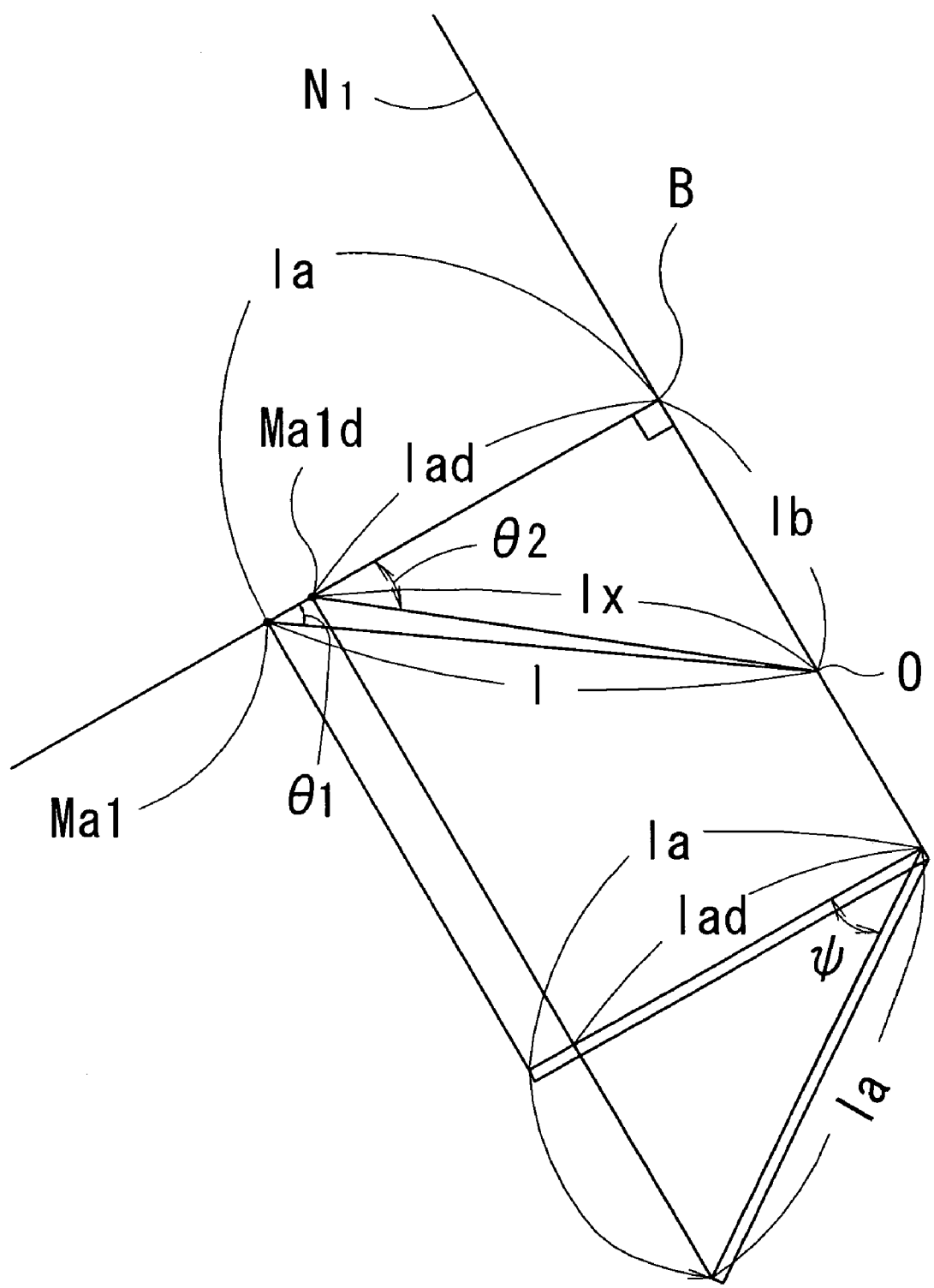
FIG. 9 is still another view describing the detection of the duction condition.

Here, the displacement (deviation) of Ma1 to Ma1d is considered. As shown in FIG. 9, assume that an intersection point of a displacement (deviation) direction of Ma1 and the axis N1 is B, and a central reference point of the duction is O (when the pupil center position is not displaced (deviated), the pupil center position EPc viewed from the Z direction is the reference point O). An angle between a segment O•Ma1 and a segment Ma1•B of a triangle O•Ma1•B is expressed as θ1. Assuming that lengths of the segment O•Ma1, the segment Ma1•B, a segment B•O and a segment Ma1d•B are l, la, lb and lad, respectively, Formulae 2-1 to 2-3 are obtained.

$$la = l \cos \theta 1 \qquad \text{Formula 2-1}$$

$$lad = la \cos \psi = l \cos \theta 1 \cos \psi \qquad \text{Formula 2-2}$$

$$lb = l \sin \theta 1 \qquad \text{Formula 2-3}$$

In addition, assuming that an angle between a segment O•Ma1d and the segment Ma1d•B of a triangle O•Ma1d•B is θ2 and a length of the segment O•Ma1d is lx, Formulae 2-4 and 2-5 are obtained.

$$lad = lx \cos \theta 2 \qquad \text{Formula 2-4}$$

$$lb = lx \sin \theta 2 \qquad \text{Formula 2-5}$$

When Formulae 2-1 to 2-5 are rearranged, Formulae 2-6 and 2-7 are obtained.

$$lx \cos \theta 2 = l \cos \theta 1 \cos \psi \qquad \text{Formula 2-6}$$

$$lx \sin \theta 2 = l \sin \theta 1 \qquad \text{Formula 2-7}$$

Figure 10:
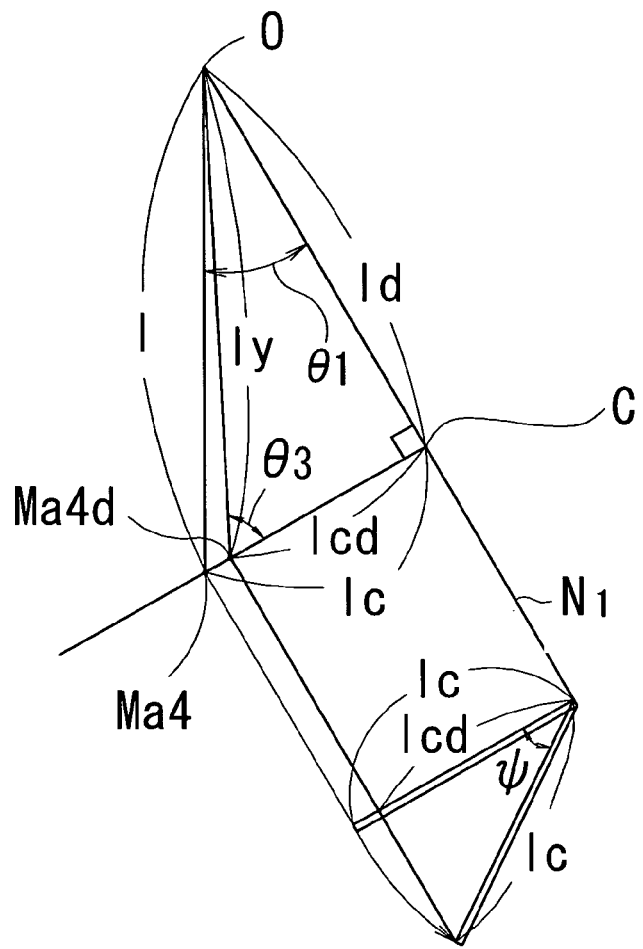
FIG. 10 is still another view describing the detection of the duction condition.

Next, the displacement (deviation) of Ma4 to Ma4d is considered. As shown in FIG. 10, assume that an intersection point of a displacement (deviation) direction of Ma4 and the axis N1 is C. An angle between a segment O•Ma4 and a segment O•C of a triangle O•Ma4•C is expressed as θ1. Assuming that lengths of the segment O•Ma4, a segment Ma4•C, the segment C•O and a segment Ma4d•C are l, lc, ld and lcd, respectively, Formulae 2-8 to 2-10 are obtained.

$$lc = l \sin \theta 1 \qquad \text{Formula 2-8}$$

$$lcd = lc \cos \psi = l \sin \theta 1 \cos \psi \qquad \text{Formula 2-9}$$

$$ld = l \cos \theta 1 \qquad \text{Formula 2-10}$$

In addition, assuming that an angle between a segment O•Ma4d and the segment Ma4d•C of a triangle O•Ma4d•C is θ3 and a length of the segment O•Ma4d is ly, Formulae 2-11 and 2-12 are obtained.

$$lcd = ly \cos \theta 3 \qquad \text{Formula 2-11}$$

$$ld = ly \sin \theta 3 \qquad \text{Formula 2-12}$$

When Formulae 2-8 to 2-12 are rearranged, Formulae 2-13 and 2-14 are obtained.

$$ly \cos \theta 3 = l \sin \theta 1 \cos \psi \qquad \text{Formula 2-13}$$

$$ly \sin \theta 3 = l \cos \theta 1 \qquad \text{Formula 2-14}$$

Further, the unknown numbers θ1, θ2 and θ3 are eliminated from Formulae 2-6, 2-7, 2-13 and 2-14 to obtain Formula 2-15, thereby the duction angle ψ is obtained.

$$\cos^2 \psi = (lx^2 + Ly^2 - l^2)/l^2 \qquad \text{Formula 2-15}$$

When ψ is obtained, the duction direction θ1 is obtained by transforming Formulae 2-6, 2-7, 2-13 and 2-14 into formula 16.

$$\cos^2 \theta 1 = (lx^2 - l^2)/(l^2 \cos^2 \psi - l^2) \qquad \text{Formula 16}$$

Figure 8:
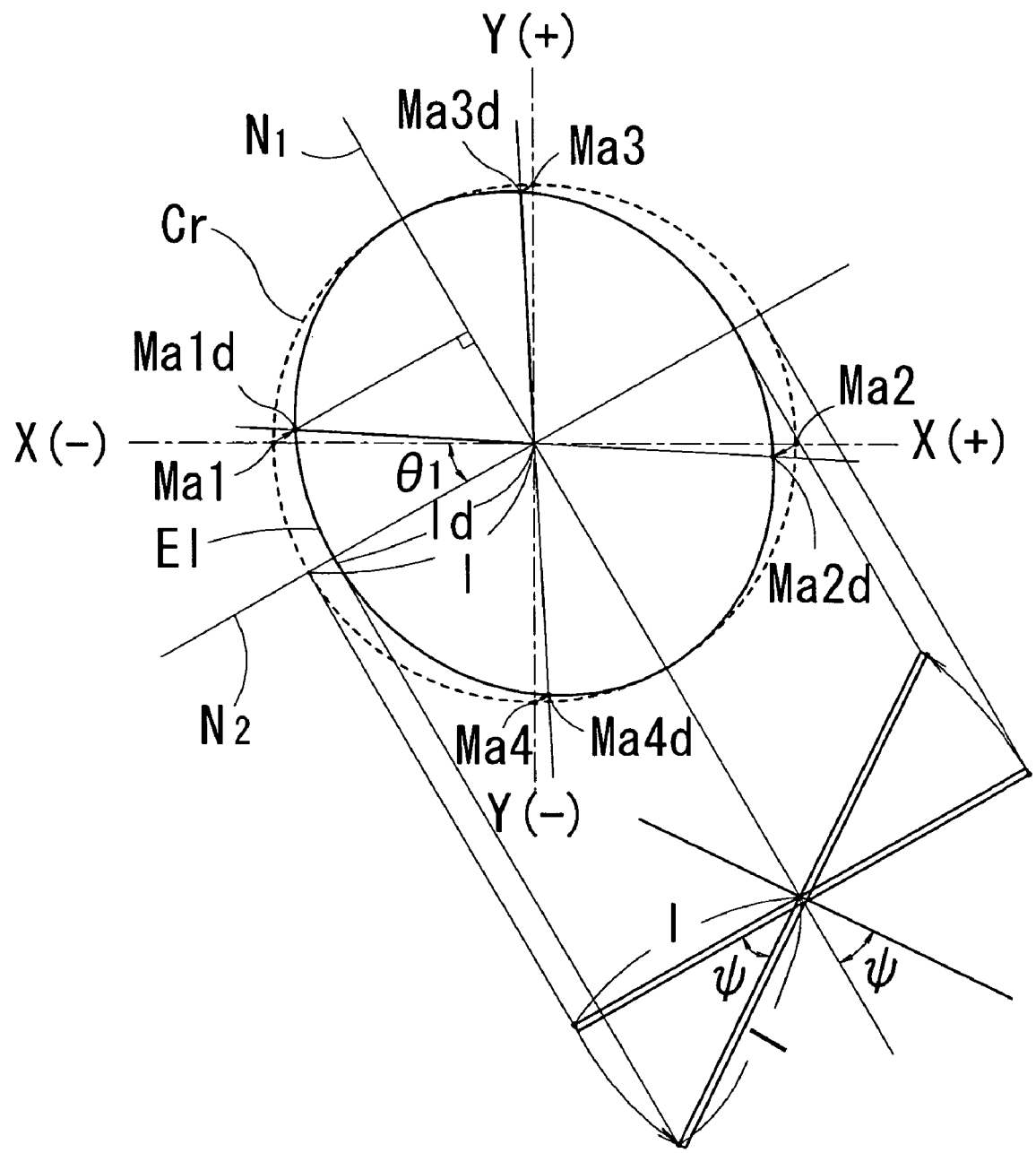
FIG. 8 is another view describing the detection of the duction condition.

Besides, the duction direction θ1 and the duction angle ψ may also be obtained as follows. In FIG. 8, assume that the detection points Ma1, Ma2, Ma3 and Ma4 of the respective marks are on a circumference of a circle Cr having the point O at its center. When the detection points Ma1, Ma2, Ma3 and Ma4 of the respective marks are displaced (deviated) to Ma1d, Ma2d, Ma3d and Ma4d, respectively, an ellipse El passing through Ma1d, Ma2d, Ma3d and Ma4d is calculated. A minor axis of the ellipse El is determined to obtain the duction direction θ1. Incidentally, the circle Cr and the ellipse El may be obtained with not necessarily four detection points, but at least three detection points. Then, the duction angle ψ is obtained from a diameter L (or a radius l) of the circle Cr and a diameter Ld of the ellipse El's minor axis (or a distance ld from the point O) which is changed from the diameter L, using Formula 1-1. When the duction angle ψ is obtained, the displacement (deviation) amount ΔL between the positions P and Pd on the cornea Ec is obtained using Formula 1-2. Further, changes in the lengths of the respective marks indicate whether the duction direction θ1 is the X(+), X(−), Y(+) or Y(−) direction. Though the above description is given under a polar coordinate system, it may be calculated by converting into a rectangular coordinate system.

In the alignment or the tracking, based on the detection results of the duction condition as above, the control unit 250 moves the optical axis SL in the X and Y directions with respect to the pupil center position detected from the image picked up by the camera 233 so as to further correct the above displacement (deviation) amount ΔL in the duction direction. Thereby, the irradiation position of the laser beam is aligned with the position P on the cornea Ec in the reference state.

Incidentally, the alignment or the tracking of the irradiation position with respect to the eye E may not necessarily be performed with reference to the pupil center position directly detected. In a case where the marks are provided, a center position of the marks may be taken as the reference. Alternatively, a position of a corneal limbus may be detected from the image of the anterior-segment, and its center position may be taken as the reference.

Figure 11:
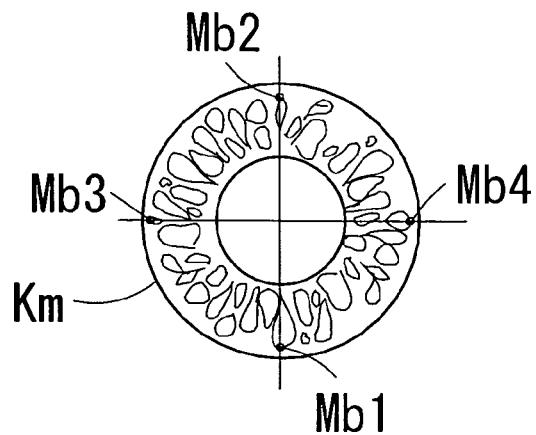
FIG. 11 is a view illustrating an example where an iris pattern is taken as a characteristic point.

In the above description, the marks are utilized for detecting the duction condition. However, another characteristic points included in the anterior-segment may also be utilized. For example, based on the images of the anterior-segment in the reference state picked up by the measurement apparatus 1 and that at the time of the surgery, positional information on respective characteristic points Mb1 to Mb4 in an iris pattern is obtained (detected) through image processing as shown in FIG. 11. In order to reduce influences of miosis or mydriasis, it is preferable that the characteristic points of the iris pattern are on the corneal limbus side. The duction condition may be detected by processing the characteristic points Mb1 to Mb4 in the iris pattern instead of the marks. In addition, the corneal limbus Km may also be used as the characteristic point. An edge position of the corneal limbus is detected through image processing, and as in the case of FIG. 8, the duction condition is obtained from the circle Cr obtained when the eye E is in the reference state and the ellipse El obtained during the surgery.

Figure 12A:
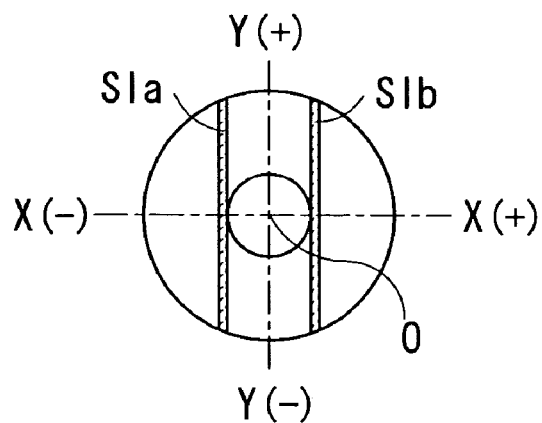
FIGS. 12A to 12C are views describing detection of a duction direction utilizing two slit images.

In a case where the marks are not utilized, a change in a length of the iris pattern or the like may be utilized for determining whether the duction is in the X(+), X(−) Y(+) or Y(−) direction. Alternatively, other information may also be utilized. In the apparatus of the present embodiment, changes in two slit images projected onto the iris from the slit projection optical systems 240a and 240b for alignment in the Z direction may be utilized. FIG. 12A shows the two slit images Sla and Slb projected onto the iris when an iris surface is horizontally positioned. When the iris surface is horizontally positioned, the two slit images Sla and Slb are parallel to each other, and have a positional relationship that they are at the same distance from the reference position O.

Figure 12B:
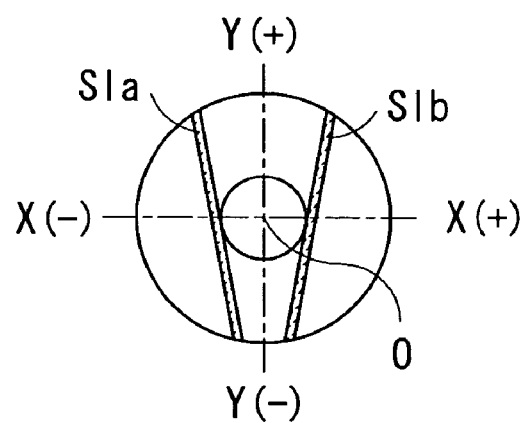
Figure 12C:
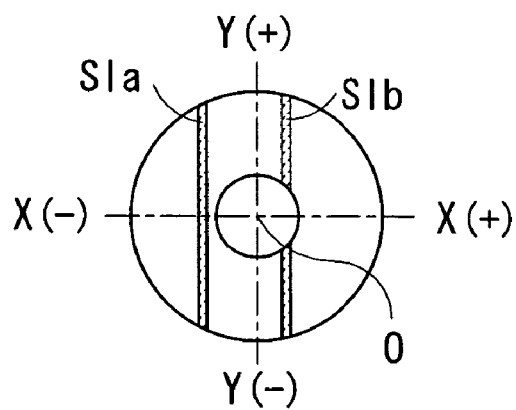

FIG. 12B shows a state where the iris surface is inclined in the Y(+) direction. The slit images Sla and Slb have such a positional relationship that a distance therebetween is greater in the Y(+) direction than in the Y(−) direction. FIG. 12C shows a state where the iris surface is inclined in the X(−) direction. The slit images Sla and Slb have an positional relationship where the distance from the reference point O to the slit image Sla is greater than that to the slit image Slb. The inclination direction may be determined based on the change in the positional relationship between the slit images Sla and Slb.

In the above description, the pupil center position is assumed not to be displaced (deviated) with respect to the reference state. However, among the patients, there is a case where a pupil area (a pupil diameter) is changed due to miosis or mydriasis under the strain, so that the pupil center position itself is displaced (deviated). In such a case, it is preferable to move the irradiation position so as to correct the displacement (deviation)

Figure 13:
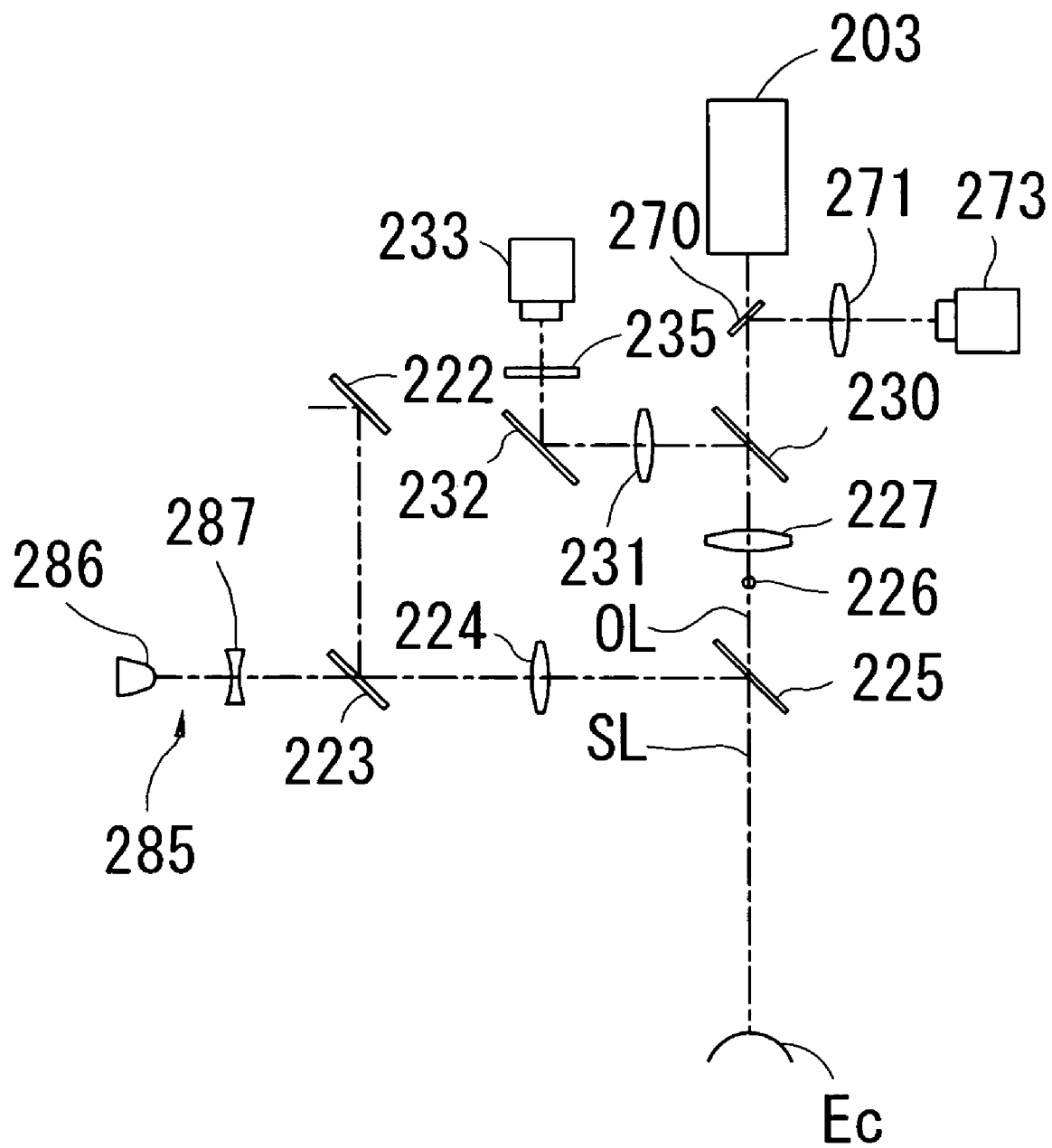
FIG. 13 is a view showing a schematic configuration of the optical system provided with a target projection optical system for forming a Purkinje's image on the patient's eye.

Hereinafter, detection of the displacement (deviation) of the pupil position due to the change in the pupil area will be described. FIG. 13 is a view showing a schematic configuration of an optical system provided with a target projection optical system for forming a Purkinje's image on the eye E in order to detect the displacement (deviation) of the pupil position. In FIG. 13, the same constitutional elements as those in FIG. 3 are partly not illustrated. The target projection optical system 285 is provided with an infrared light source 286 and a lens 287 that are arranged behind the mirror 223. The mirror 223 is a dichroic mirror which reflects the excimer laser beam and transmits the infrared light. Further, the dichroic mirror 225 has a property of reflecting a part of the infrared light. The light emitted from the infrared light source 286 is made parallel by the lenses 287 and 224, and is reflected by the mirror 225 to a direction of the optical axis SL toward the cornea Ec. Formed on the cornea Ec is a corneal reflex (Purkinje's image) to be picked up by the camera 233. As shown in FIG. 14A, a positional relationship between the reflex Pr and the pupil center position EPc is detected from the image of the anterior-segment picked up by the camera 233.

Besides, also in the measurement apparatus 1, light for forming a similar corneal reflex is projected from an image-pickup optical axis direction, and the positional relationship between the reflex Pr and the pupil center position Epc is previously obtained by picking up the image of the anterior-segment of the eye E before the surgery. This positional relationship is taken as the reference state.

Here, assuming that the reflex Pr and the pupil center position EPc are in agreement in the reference state, there are two types of displacement (deviation) of the pupil center position EPc from the reflex Pr detected during the surgery; the displacement due to the duction and that due to the displacement of the pupil center position itself. The displacement (deviation) amount due to the duction is obtained from FIG. 14A as:

$$\Delta X = R \sin \psi - \Delta L.$$

1θ4 and ΔL are values obtained in the duction detection mentioned above. R is a corneal curvature, which is obtained from the measurement results of the eye E.

Assume that Δx is a displacement (deviation) amount of the pupil center position EPc from the reflex Pr which is detected during the surgery. And if ΔX and Δx are compared and detected to be approximately equal, the displacement (deviation) may be judged that it is due only to the duction.

When ΔX and Δx are not equal, a difference therebetween may be regarded as the displacement (deviation) of the pupil center position as compared to the reference state. FIG. 14B shows a case where the duction does not occur (ΔX=0), and the pupil center position EPc is displaced (deviated) due to the change in the pupil diameter.

Therefore, if the irradiation position of the laser beam is moved so as to correct the difference between ΔX and Δx, the irradiation of the laser beam may be performed accurately also in the case of the displacement (deviation) of the pupil center position. Incidentally, as the displacement (deviation) of the pupil center position increases, the error in the alignment of the irradiation position also increases. Thus, the applicability of the laser irradiation is judged based on whether the displacement (deviation) of the pupil center position is in a predetermined allowable range or not, and in the event that the deviation is beyond the predetermined allowable range, the laser irradiation is preferably suspended. At the time of the suspension of the laser irradiation, the control unit 250 controls to insert the safety shutter 280 into the optical path.

Further, since the duction may be judged to occur due to the intense strain on the patient, it is preferable also for the duction that the applicability of the laser irradiation is judged based on whether the displacement (deviation) of the pupil center position is in a predetermined allowable range or not, and in the event that the deviation is beyond the predetermined allowable range, the laser irradiation is preferably suspended.

Various modifications may be applied to the above-described preferred embodiment. For example, the irradiation optical system of the laser beam may have a constitution where a scanning mirror (it may consist of two Galvano mirrors) for scanning a laser beam formed into a small spot of about 0.1 mm to 1.0 mm in two-dimensional directions of the X and Y directions. The movement of the irradiation position of the laser beam in the tracking may be performed by driving and controlling the scanning mirror to move the irradiation reference axis. Further, in the case of the irradiation optical system employing a large beam and an aperture with a variable opening diameter, a mechanism for decentering and moving an axis of the projecting lens may be provided to move the irradiation position of the laser beam.

Incidentally, though the irradiation optical system side is moved for the alignment and the tracking in the preferred embodiment, the patient's eye side maybe moved (for example, by movement of the bed 290 and the like).

As described above, the present invention enables more accurate irradiation of the laser beam onto the desired position on the cornea even in the event of the duction and further in the event of the displacement (deviation) of the pupil position.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A corneal surgery apparatus comprising:
   an irradiation optical system having an irradiation reference axis, for irradiating onto a cornea a laser beam which brings about ablation of the cornea;
   alignment means for moving the irradiation optical system in X and Y directions with respect to a patient's eye to perform alignment in the X and Y directions and moving the irradiation optical system in a Z direction with respect to the patient's eye to perform alignment in the Z direction;
   detection means for detecting one of a pupil and a corneal limbus by picking up an image of an anterior-segment of the patient's eye and performing image processing thereon;
   a memory which stores a center and shape of the one of the pupil and the corneal limbus detected when the alignment in the X, Y and Z directions is performed;
   calculation means for obtaining X, Y positional deviation information on the eye based on change of a center of the one of the pupil and the corneal limbus detected during surgery from the center of the one of the pupil and the corneal limbus stored in the memory, then obtaining duction information on an eyeball based on change of a shape of the one of the pupil and the corneal limbus detected during the surgery from the shape of the one of the pupil and the corneal limbus stored in the memory and change in a slit image projected onto an iris from a symmetric direction so as to intersect with the irradiation optical axis, and then obtaining alignment deviation in the X and Y directions based on the obtained X, Y positional deviation information and the obtained duction information; and
   control means for operating the alignment means to perform the alignment in the X and Y directions based on the obtained alignment deviation in the X and Y directions.

2. A corneal surgery apparatus comprising:
   an irradiation optical system having an irradiation reference axis, for irradiating onto a cornea a laser beam which brings about ablation of the cornea;
   alignment means for moving the irradiation optical system in X and Y directions with respect to a patient's eye to perform alignment in the X and Y directions and moving the irradiation optical system in a Z direction with respect to the patient's eye to perform alignment in the Z direction;
   detection means for detecting one of a pupil and a corneal limbus by picking up an image of an anterior-segment of the patient's eye and performing image processing thereon;
   a memory which stores a center and shape of the one of the pupil and the corneal limbus detected when the alignment in the X, Y and Z directions is performed;
   calculation means for obtaining X, Y positional deviation information on the eye based on change of a center of the one of the pupil and the corneal limbus detected during surgery from the center of the one of the pupil and the corneal limbus stored in the memory, then obtaining duction information on an eyeball based on change of a shape of the one of the pupil and the corneal limbus detected during the surgery from the shape of the one of the pupil and the corneal limbus stored in the memory and change of at least three marks provided to a sclera and extending in meridional directions, and then obtaining alignment deviation in the X and Y directions based on the obtained X, Y positional deviation information and the obtained duction information; and
   control means for operating the alignment means to perform the alignment in the X and Y directions based on the obtained alignment deviation in the X and Y directions.

* * * * *